United States Patent
Short et al.

(10) Patent No.: US 6,863,691 B2
(45) Date of Patent: Mar. 8, 2005

(54) ANKLE IMPLANT

(76) Inventors: Timothy J. Short, 3 S. Valencia Dr., Davie, FL (US) 33324; Ha Van Vo, 864 SW. 64th Ter., North Lauderdale, FL (US) 33068

( * ) Notice: Subject to any disclaimer, the term of this patent is extended or adjusted under 35 U.S.C. 154(b) by 165 days.

(21) Appl. No.: 10/134,093

(22) Filed: Apr. 29, 2002

(65) Prior Publication Data

US 2003/0204265 A1 Oct. 30, 2003

(51) Int. Cl.[7] .................................................. A61F 2/42
(52) U.S. Cl. .................................................. 623/21.18
(58) Field of Search ........................... 623/21.18, 21.11, 623/18.11, 21.19, 20.18, 20.19, 20.2, 11.11, 13.11, 13.12, 13.13, 13.14, 16.11

(56) References Cited

U.S. PATENT DOCUMENTS

| | | | | |
|---|---|---|---|---|
| 3,839,742 A | * | 10/1974 | Link ........................ | 623/21.18 |
| 3,872,519 A | * | 3/1975 | Giannestras et al. ...... | 623/21.18 |
| 3,889,300 A | * | 6/1975 | Smith ....................... | 623/21.18 |
| 3,975,778 A | * | 8/1976 | Newton, III .............. | 623/21.18 |
| 4,069,518 A | * | 1/1978 | Groth et al. .............. | 623/21.18 |
| 4,470,158 A | * | 9/1984 | Pappas et al. ............ | 623/20.21 |
| 5,326,365 A | * | 7/1994 | Alvine ..................... | 623/21.18 |
| 5,658,341 A | * | 8/1997 | Delfosse ................... | 623/20.32 |
| 5,824,106 A | * | 10/1998 | Fournol .................... | 623/21.18 |
| 6,409,767 B1 | * | 6/2002 | Perice et al. ............. | 623/21.18 |

OTHER PUBLICATIONS

F.F. Buechel M.D. & M.J. Pappas Ph.D "The Buechel–Pappas Total Ankle Replacement System" 4 pages—Endotec, Inc. Feb. 28, 2001.
"Link® S.T.A.R.® Total Ankle Joint Prosthesis" 1 page—www.linkhh.de/link–en/produkte/fuss/star.
"Ankle Joint Replacement Components" 2 pages—www.allaboutarthritis.com.
Orthopaedic Associates of Grand Rapids, P.C. "Ankle Replacement" 3 pages—www.oagr.com/ankle_replacement.

* cited by examiner

*Primary Examiner*—Pedro Philogene
(74) *Attorney, Agent, or Firm*—Oltman, Flynn & Kubler

(57) ABSTRACT

An ankle implant having a tibial component with a bottom groove, a talar component with a convex dome on top, and a bearing component slidably insertable into the bottom groove in the tibial component and having a concave bottom recess receiving the top dome of the talar component. The tibial component is channel-shaped, with a flat bottom wall for reception in a corresponding surgically prepared recess in the bottom of the patient's tibia, an anteriorly inclined posterior end wall projecting up from its bottom wall, a taller anterior end wall perpendicular to its bottom wall, and a rounded groove on the inside at the juncture between the anterior and bottom walls. The talar component has a cross-shaped segment on the bottom for reception in a corresponding surgically prepared recess in the top of the patient's talus.

17 Claims, 4 Drawing Sheets

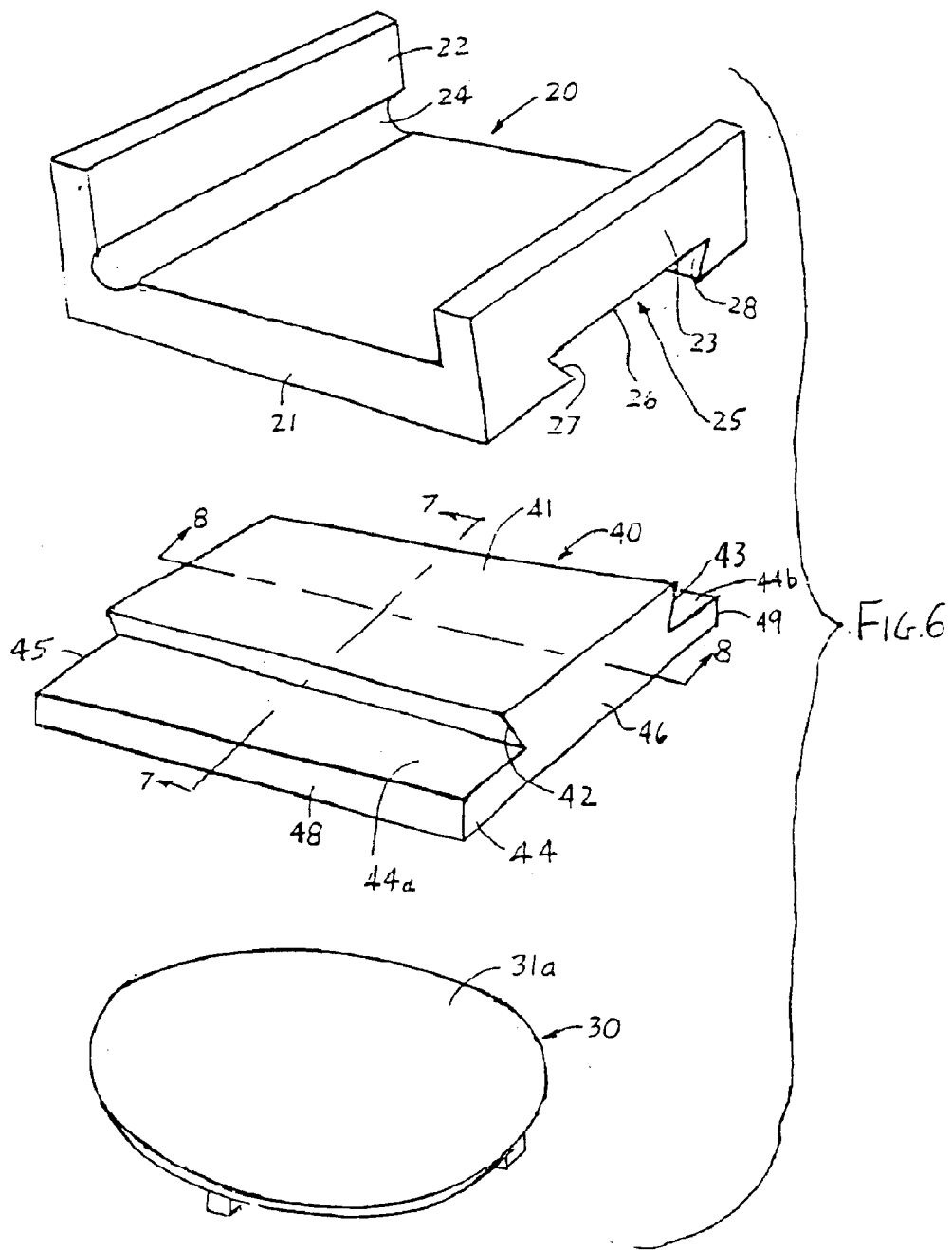

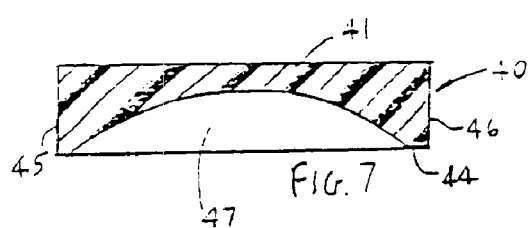
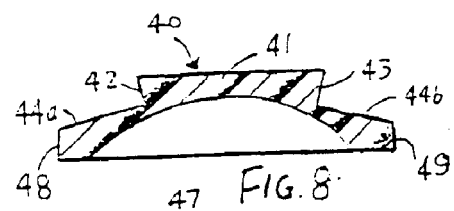
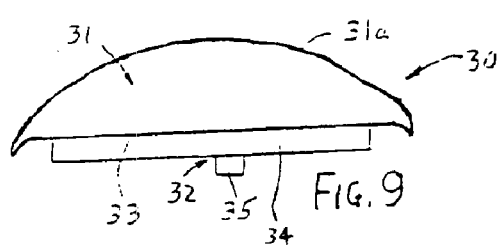
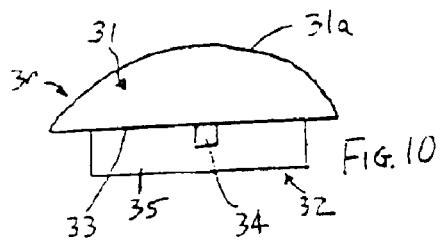
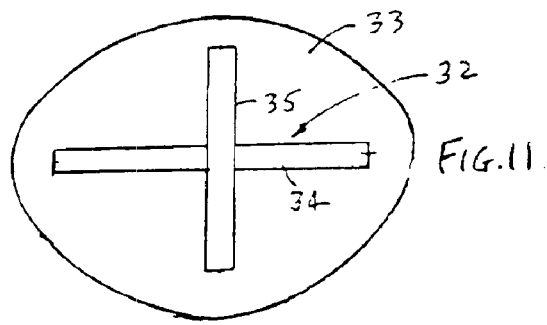

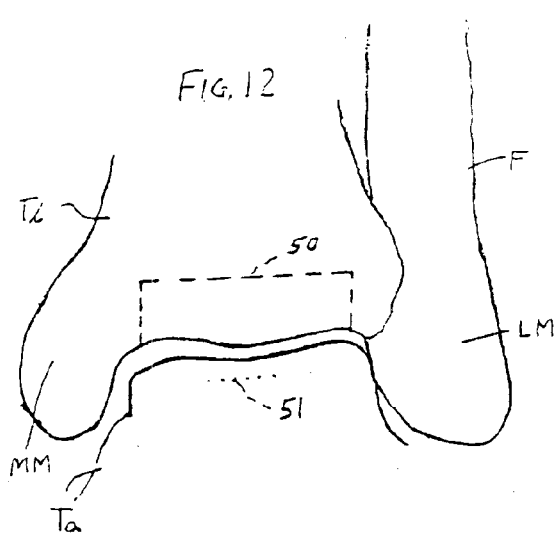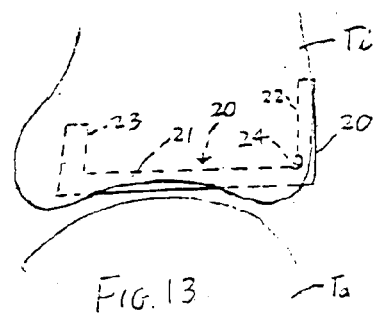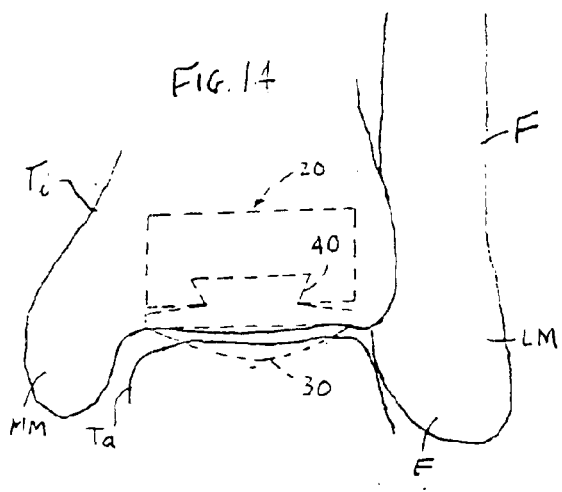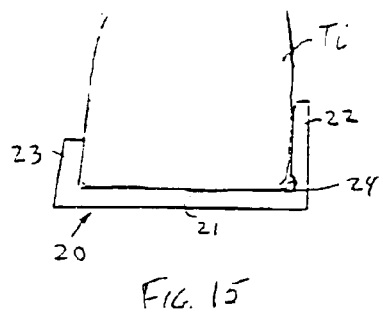

ANKLE IMPLANT

BACKGROUND OF THE INVENTION

1. Field of the Invention

This invention relates to an implant for insertion between a person's tibia and talus to enable the ankle to function substantially normally and overcome or alleviate the effects of arthritis or avascular necrosis in the ankle joint.

2. Prior Art

The Buechel-Pappas Total Ankle Replacement System comprises:

a tibial component with an upwardly-projecting fixturing stem that extends centrally up into the patient's tibia in the marrow region, and a bottom plate located just below the tibia and presenting a flat bearing surface on the bottom;

a meniscus bearing component with a flat bearing surface at the top that slidably engages the tibial component plate from below, and a bottom bearing surface of compound curvature; and a talar component with a top bearing surface of compound curvature substantially complementary to that of the bottom surface of the bearing component, and a pair of downwardly-projecting fixation fins on the bottom for reception in corresponding channels prepared in the top of the patient's talus by the surgeon.

The Scandinavian Total Ankle Replacement (STAR) is broadly similar to the Buechel-Pappas system but differs from it in the compound curvature interface between the bottom of its bearing component and the top of its talar component, as well as in the mode of attaching its tibial component to the patient's tibia., which in the Scandinavian system is by means of attachment members of stepped cylindrical configuration on the top of the tibial component.

In the Buechel-Pappas and STAR implants the compound curvatures of the respective bearing and talar component interfaces tend to inhibit the natural movements of inversion and eversion in the ankle joint. In addition, some patients have experienced loosening of the tibial component of the implant.

The Agility™ Total Ankle system has its bearing component affixed to the tibial component and presenting a generally rectangular, round-cornered recess on the bottom which is substantially flat across most of its extent for snugly receiving a complementary talar component. Both the tibial component and the talar component have fixturing stems for implantation respectively in the patient's tibia and talus. This procedure requires resectioning a relatively large amount of bone, which may cause bone weakening and lead to bone fracture.

SUMMARY OF THE INVENTION

The present invention is directed to a novel ankle implant which requires minimal bone removal before its tibial and talar components are applied to the patient's tibia and talus, respectively. An important feature of this invention is the novel and simplified, yet effective, curvature of the interface between its talar component and its bearing component, which is affixed to its tibial component.

A principal object of this invention is to provide a novel ankle implant for insertion in the ankle joint of a patient with osteoarthritis, rheumatoid arthritis, trauma-related Arthritis, or avascular necrosis (ostenonecrosis) to enable the patient to recover full ordinary use of the ankle joint with no pain, or greatly reduced pain.

Another object of this invention is to provide a novel ankle implant with a highly effective attachment of its tibial component to the patient's tibia.

Another object of this invention is to provide a novel ankle implant with a convenient arrangement for coupling its bearing component to its tibial component while sliding it between the tibial and talar components previously applied respectively to the patient's tibia and talus.

Yet another object of this invention is to provide an ankle implant with a novel arrangement for applying its talar component to the patient's talus.

Further objects and advantages of the invention will be apparent from the following detailed description of a presently preferred embodiment thereof, illustrated in the accompanying drawings.

All references herein to direction (e.g., "up") or position (e.g., "lower") relate to a patient in a standing position

BRIEF DESCRIPTION OF THE DRAWINGS

FIG. 6 is an exploded perspective view of the present ankle implant;

FIG. 7 is a lateral section of the bearing component of the present implant, taken along the line 7—7 in FIG. 6;

FIG. 8 is a longitudinal section of the bearing component, taken along the line 8—8 in FIG. 6;

FIG. 9 is an anterior elevation of the talar component of the present implant;

FIG. 10 is a lateral elevation of this talar component; and

FIG. 11 is a bottom plan view of this talar component.

FIG. 12 is an anterior-posterior view of the right tibia and talus, showing in dashed lines a cut that the surgeon will make in the lower end of the tibia for receiving the tibial component of the present implant and showing in dotted lines the depth of a cross-cut the surgeon will make in the top of the talus for receiving the talar component of the present implant;

FIG. 13 is a view of right ankle bones similar to FIG. 4 with the tibial component of the present implant (in phantom) shown in place;

FIG. 14 is a view similar to FIG. 12 with the present implant in place; and

FIG. 15 is a longitudinal vertical section through the tibial component of the present implant applied to the tibia.

DETAILED DESCRIPTION OF THE INVENTION

Before explaining the present invention in detail it is to be understood that the invention is not limited in its application to the particular arrangement shown and described herein since the invention is capable of other embodiments. Also, the terminology used herein is for the purpose of description and not of limitation.

Figure 1:
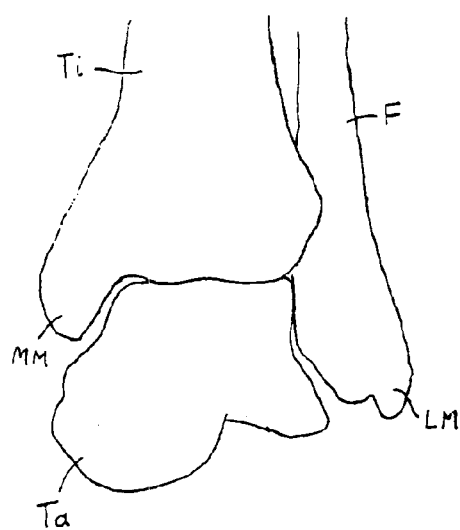
FIG. 1 is an elevational view of a patient's left talus and the lower ends of the left tibia and fibula, articulated, from the front.
Figure 2:
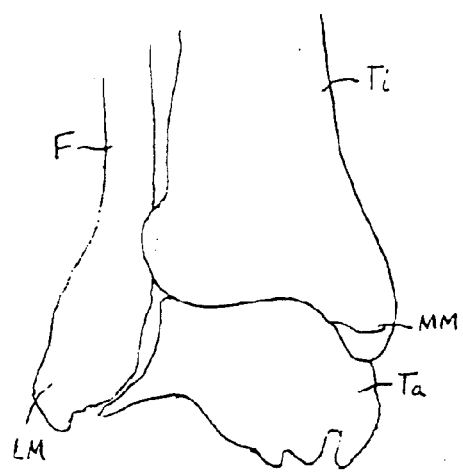
FIG. 2 is a similar view of these bones from the rear.
Figure 3:
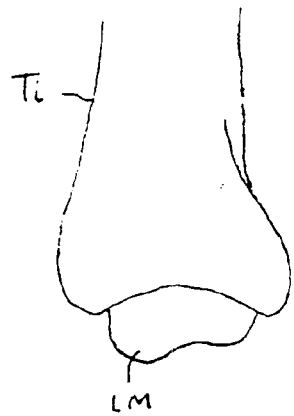
FIG. 3 is an elevation of the left tibia from the lateral side.
Figure 4:
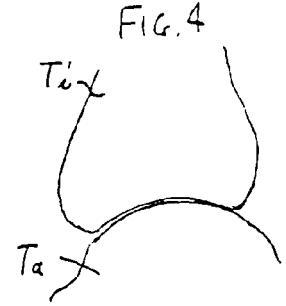
FIG. 4 is a sagittal section of a patient's right foot through the second toe, showing the top of the talus and the lower end of the tibia from the medial side.
Figure 5:
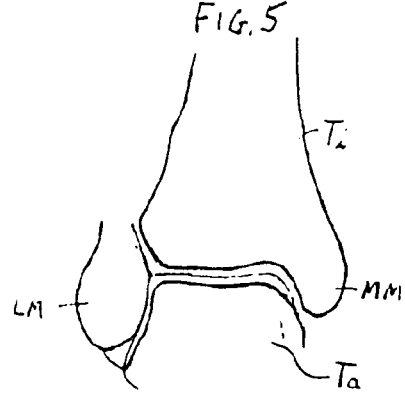
FIG. 5 is a section of the left ankle joint a short distance in front of the rear of the talus.

FIGS. 1–5 show various views of a person's tibia Ti, talus Ta and fibula F at the ankle joint. The medial malleolus of the tibia is designated MM, and the lateral malleolus of the fibula is designated LM.

In accordance with the present invention, the ankle implant consists of a tibial component 20 (FIG. 6) for attachment to the lower end of the patient's tibia, a talar component 30 (FIGS. 6, 9, 10 and 11) for seating engagement in the top of the talus, and a bearing component 40 (FIGS. 6, 7 and 8) for attachment to the tibial component and sandwiched engagement between the tibial and talar components.

Referring to FIG. 6, the tibial component 20 of this implant is of a suitable titanium alloy, preferably. The surfaces of this component are roughened to encourage stability of its implantation on the patient's tibia with bone growth and healing. It is generally channel-shaped, with a flat rectangular bottom wall 21, a flat rectangular anterior end wall 22 extending perpendicularly up from the bottom wall 21 at its anterior end, and a flat rectangular posterior end wall 23 extending up from the opposite, posterior end of the bottom wall at a slight inclination toward the anterior end wall. Preferably, the posterior end wall 23 extends at an angle of 85 degrees to the bottom wall. The oblique angularity of this end wall helps stabilize the tibial component 20 at its posterior end on the pateint's tibia Ti. The anterior end wall 22 has a greater height than the posterior end wall 23. At the juncture between the bottom wall and the anterior end wall, the tibial component present a cut-away, rounded groove 24 of cylindrical configuration at its inside corner across its complete width. This groove facilitates bone growth to stabilize the anterior end of the tibial component 20 of the implant on the patient's tibia Ti. At the bottom, along its entire length the tibial component is formed with a relatively shallow downwardly-facing groove or recess 25 located midway between its opposite sides. This groove is defined by a relatively wide flat top surface 26, which extends parallel to the flat top and bottom faces of the bottom wall 21, and downwardly and inwardly inclined opposite side surfaces 27 and 28, so that the groove is progressively wider up from the bottom surface of the tibial component. Preferably, the side surfaces 27 and 28 extend at opposite 75 degree angles to the top surface 26 of groove 25.

The bearing component 40 of the present implant (FIGS. 6, 7 and 8) is of ultra-high molecular weight polyethylene or other suitable material with self-lubricating properties. It has a top segment 41 that is shaped and dimensioned to be snugly but slidably received in the complementary bottom groove 25 in the above-described tibial component 20. Top segment 41 has opposite side edges 42 and 43 with respective inclinations matching those of the corresponding opposite side surfaces 27 and 28 of the tibial component's bottom groove 25. The bearing component has a bottom segment 44 which is wider than its top segment 41 and projects on opposite sides of it along the entire length of this component from a flat anterior end surface 45 to a flat posterior end surface 46. On one side of the top segment 41, the bottom segment 44 presents an upper surface 44a that has a slight downward inclination laterally outward, as best seen in FIG. 8. Similarly, on the opposite side of the top segment, the bottom segment presents an upper surface 44b with a slight downward inclination laterally away from the top segment 41. After slidable insertion of its top segment 41 into the bottom groove in the tibial component, the bearing component is affixed to the tibial component by a titanium screw or other fastener (not shown). The bearing component 40 is formed with a downwardly-facing, concave, bottom recess 47 of continuous rounded curvature both lengthwise between its anterior and posterior end faces 45 and 46 (FIG. 7) and laterally between its opposite side faces 48 and 49 (FIG. 8). Recess 47 is oblong and generally elliptical overall, having a greater dimension lengthwise of the bearing component (FIG. 7) than laterally of it (FIG. 8).

FIGS. 9, 10 and 11 show the talar component 30 of the present implant, which preferably is of titanium alloy. This component has a convex top segment or dome 31 whose top surface 31a over its entire extent has a continuous rounded curvature substantially matching that of the bottom recess 47 in the bearing component 40 both longitudinally and laterally to allow a full range of movement like that of a natural ankle joint. The dome or top segment 31 of the talar component is slightly larger than the bearing component 40 both longitudinally and laterally, so that its convex top surface 31a projects beyond the bearing component both longitudinally and laterally in all positions of the talar component 30 with respect to the tibial component 20, whether the patient is standing or walking, for example. The talar component has a bottom segment 32 FIG. 12) of generally cross-shaped configuration which projects down from a flat bottom face 33 of its top segment 31. Bottom segment 32 is made up of an elongated longitudinal element 34 of rectangular cross-section which located on the longitudinal axis of the talar component 30 and an elongated lateral element 35 of rectangular cross-section located on its lateral axis. As shown, the lateral element 35 projects farther down than the longitudinal element 34 but, if desired, they may have co-planar bottom faces instead.

To accommodate the tibial component 20 of the implant, the surgeon cuts a flat-sided recess substantially 1 cm. deep (i.e., upward) in the bottom of the patient's tibia Ti over its complete anterior-to-posterior extent. The position of this recess in the tibia is shown in dashed lines at 50 in FIG. 12. The depth of this recess is greater than the thickness of the bottom wall 21 of the implant's tibial component 20. The width of this recess (i.e., from the lateral side to the medial side of the patient's foot) is such that it does not invade the medial malleolus MM of the tibia Ti, and it is not cut into the lateral malleolus LM of the fibula F. The surgeon places the tibial component 20 of the present implant underneath the tibia Ti with the bottom wall 21 of the tibial component underlying the recess the surgeon has cut in the bottom of the tibia, with the anterior end wall 22 next to the anterior surface of the tibia at the anterior end of this tibia recess, and with the posterior end wall 23 next to the posterior surface of the tibia at the posterior end of this tibia recess. The length of the bottom wall 21 of tibial component 20 between its anterior and posterior end walls is such that when the surgeon uses a hammer to apply the tibial component to the patient's tibia, its bottom wall 21 is forced snugly into the surgically prepared bottom recess in the tibia and its end walls 22 and 23 tightly grip the tibia between them. This gripping action is enhanced by the anterior inclination of the posterior end wall 23 of the tibial component.

To accommodate the talar component 30 of the present implant the surgeon cuts a cross-shaped groove or recess in the top of the patient's talus Ta that is complementary to the cross-shaped bottom segment 32 of the implant's talar component 30, so that the talar component fits snugly on top of the talus and presents its convex top segment or dome 31 immediately above the talus. The bottom of the surgically prepared groove or recess in the talus is indicated at the dotted lines 51 in FIG. 12.

Following the foregoing steps, the surgeon inserts the top segment 41 of bearing component 40 endwise into the bottom groove 25 in tibial component 20 and slides the bearing component 40 lengthwise of the tibial component 20 between it and the talar component 30 until the components of the implant fit together as shown in dashed lines in FIG. 14. Finally, the surgeon attaches the bearing component 40 to the tibial component 20 with a titanium screw so that in the use of the implant there is no relative movement between these two components, and the only bearing interface where relative movement takes in the implant is at the convex top surface 31*a* on the dome 31 of the talar component and the concave bottom recess 47 in the bearing component. This provides an effective arrangement of optimum structural simplicity for enabling the patient's full range of movement in the ankle joint.

We claim:

1. An ankle implant comprising a tibial component for attachment to the lower end of the patient's tibia; a bearing component of anti-friction material fixedly attached to said tibial component and extending therebelow; said bearing component having anterior and posterior end faces, opposite side faces, and a bottom face of continuous concave curvature both longitudinally between said end faces and laterally between said opposite side faces;

and a talar component having an oblong periphery and a top face of continuous convex curvature substantially matching that of said bottom face of the bearing component both longitudinally and laterally to allow a full range of movement like that of a natural ankle, said talar component having attachment means for seating it on top of a patient's talus; wherein said tibial component is substantially channel-shaped, with a bottom wail shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess.

2. An ankle implant according to claim 1, wherein said anterior end wall of the tibial component extends farther up from its bottom wall than said posterior end wall.

3. An ankle implant comprising:

a talar component having an oblong periphery and a top face of continuous convex curvature both longitudinally and laterally, said talar component having attachment means for seating it on top of a patient's talus;

a tibial component for attachment to the lower end of the patient's tibia, said tibial component being substantially channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess, said anterior end wall of the tibial component extending farther up from its bottom wall than said posterior end wall, said tibial component presenting a recess on the inside of the juncture between its anterior end wall and its bottom wall to facilitate bone growth for holding the tibial component in place on the tibia;

and a bearing component of anti-friction material fixedly attached to said tibial component and extending therebelow, said bearing component having a bottom face of continuous concave curvature substantially complementary to and slidably engaging said convex top face of said talar component both longitudinally and laterally to enable corresponding angular movement of said talar component with respect to said tibial component.

4. An ankle implant according to claim 3, wherein said posterior end wall of the tibial component inclines toward said anterior end wall to enhance the grip of the tibial component on the patient's tibia.

5. An ankle implant according to claim 4, wherein said tibial component has a downwardly-facing longitudinal groove in its bottom wall, and said bearing component has a top segment shaped and dimensioned to be snugly but slidably inserted longitudinally into said groove in the bottom wall of the tibial component.

6. An ankle implant comprising:

a talar component having an oblong periphery and a top face of continuous convex curvature both longitudinally and laterally, said talar component having attachment means for seating it on top of a patient's talus;

a tibial component for attachment to the lower end of the patient's tibia, said tibial component being substantially channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess, said posterior end wall of the tibial component inclining toward said anterior end wall to enhance the grip of the tibial component on the patient's tibia, said tibial component having a downwardly-facing longitudinal groove in its bottom wall, and said bearing component having a top segment shaped and dimensioned to be snugly but slidably inserted longitudinally into said groove in the bottom wall of the tibial component.

7. An ankle implant according to claim 6, wherein said anterior wall of the tibial component extends farther up from its bottom wall than said posterior end wall.

8. An ankle implant according to claim 7, wherein said tibial component presents a recess on the inside of the juncture between its anterior end wall and its bottom wall to facilitate bone growth for holding the tibial component in place on the tibia.

9. An ankle implant according to claim 1, wherein said attachment means on said talar component is a substantially cross-shaped downwardly projecting segment on the bottom thereof for seating engagement in a surgically prepared complementary recess in the top of the patient's talus.

10. An ankle implant according to claim 5, wherein said attachment means on said talar component is a substantially cross-shaped downwardly projecting segment on the bottom thereof for seating engagement in a surgically prepared complementary recess in the top of the patient's talus.

11. An ankle implant comprising a talar component for seating engagement on top of a patient's talus, a tibial component for attachment to the lower end of the patient's tibia, and a bearing component of anti-friction material engaged between said tibial component and said talar component, said tibial component being substantially channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess.

12. An ankle implant comprising a talar component for seating engagement on top of a patient's talus, a tibial component for attachment to the lower end of the patient's tibia, and a bearing component of anti-friction material engaged between said tibial component and said talar component, said tibial component being substantially channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess, said anterior wall of the tibial component extending farther up from its bottom wall than said posterior end wall.

13. An ankle implant comprising a talar component for seating engagement on top of a patient's talus, a tibial component for attachment to the lower end of the patient's tibia, and a bearing component of anti-friction material engaged between said tibial component and said talar component, said tibial component being substantially channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess, said tibial component presenting a recess on the inside of the juncture between its anterior end wall and its bottom wall to facilitate bone growth for holding the tibial component in place on the tibia.

14. An ankle implant according to claim 13, wherein said posterior end wall of the tibial component inclines toward said anterior end wall to enhance the grip of the tibial component on the patient's tibia.

15. An ankle implant according to claim 12, wherein said posterior end wall of the tibial component inclines toward said anterior end wall to enhance the grip of the tibial component on the patient's tibia.

16. An ankle implant comprising a talar component for seating engagement on top of a patient's talus, a tibial component for attachment to the lower end of the patient's tibia, and a bearing component of anti-friction material engaged between said tibial component and said talar component, said tibial component being substantially-channel-shaped, with a bottom wall shaped and dimensioned for snug reception in a surgically prepared recess in the bottom of the patient's tibia from its anterior surface to its posterior surface, and anterior and posterior end walls extending up from said bottom wall at its opposite ends for tight engagement respectively with said anterior and posterior surfaces of the patient's tibia just above said recess, said posterior end wall of the tibial component inclining toward said anterior end wall to enhance the grip of the tibial component on the patient's tibia.

17. An ankle implant according to claim 11, wherein said talar compoent has a substantially cross-shaped downwardly projecting segment on the bottom thereof for seating engagement in a surgically prepared complementary recess in the top of the patient's talus.

* * * * *